United States Patent [19]

Gergely et al.

[11] Patent Number: 5,593,693
[45] Date of Patent: Jan. 14, 1997

[54] EFFERVESCENT MIXTURE WITH ALKALI METAL SALTS OR LYSINATES OF ACIDIC, INSOLUBLE OR SLIGHTLY SOLUBLE ACTIVE INGREDIENTS

[75] Inventors: Gerhard Gergely, Gartengasse 8, A-1053 Vienna; Thomas Gergely, Vienna; Irmgard Gergely, Vienna; Stefan Gergely, Vienna, all of Austria

[73] Assignee: Gerhard Gergely, Australia

[21] Appl. No.: 301,970

[22] Filed: Sep. 7, 1994

[30] Foreign Application Priority Data

Sep. 7, 1993 [CH] Switzerland ............... 2652/93

[51] Int. Cl.⁶ ................................. A61K 9/46
[52] U.S. Cl. ............ 424/464; 424/466; 424/439; 424/715; 424/717; 514/960; 514/974; 514/975
[58] Field of Search ................ 424/464, 466, 424/439, 715, 717; 514/960, 974, 975

[56] References Cited

U.S. PATENT DOCUMENTS

| | | | |
|---|---|---|---|
| 4,678,661 | 7/1987 | Gergely et al. | 424/44 |
| 4,888,177 | 12/1989 | Gergely et al. | 424/466 |
| 5,064,656 | 11/1991 | Gergely et al. | 424/463 |
| 5,306,506 | 4/1994 | Zema et al. | 424/466 |
| 5,415,870 | 5/1995 | Gergely et al. | 424/466 |

FOREIGN PATENT DOCUMENTS

| | | |
|---|---|---|
| 2002732 | 11/1989 | Canada . |
| 0369228 | 5/1990 | European Pat. Off. . |
| 9300886 | 1/1993 | Germany . |

*Primary Examiner*—James J. Seidleck
*Assistant Examiner*—Michael A. Williamson
*Attorney, Agent, or Firm*—Ostrolenk, Faber, Gerb & Soffen, LLP

[57] ABSTRACT

The effervescent mixture contains at least one acidic, insoluble or slightly soluble pharmaceutical active ingredient in the form of its soluble alkali metal salt or lysinate, which is present as an intimate mixture with the alkaline component and preferably coats the particles of the alkaline component of the effervescent system, for example sodium bicarbonate and/or sodium carbonate. Both components in very finely powdered form may also be present as granules, with the aid of a binder. In particular, the effervescent mixture contains, per 100 parts of active ingredient, at least 0.5 part, preferably 1 to 3 parts, of a surfactant, in particular dioctyl sulfosuccinate, and/or at least 1 part, preferably 3 to 5 parts, of a binder or suspending agent, in particular polyvinylpyrrolidone. The acidic component of the effervescent system is passivated on the surface.

19 Claims, No Drawings

EFFERVESCENT MIXTURE WITH ALKALI METAL SALTS OR LYSINATES OF ACIDIC, INSOLUBLE OR SLIGHTLY SOLUBLE ACTIVE INGREDIENTS

BACKGROUND OF THE INVENTION

The invention relates to effervescent mixtures containing at least one acidic, insoluble or slightly soluble pharmaceutical active ingredient in the form of its soluble alkali metal salt or lysinate. Such pharmaceutical active ingredients are, for example, organic derivatives of acetic acid or propionic acid, for example ibuprofen, naproxen, diclofenac, butabarbital, phenobarbital, cefazolin, diatrizoate, ethacrynate, flurbiprofen, sulfacetamide or hetacillin.

The acidic active ingredients cannot, as a rule, be obtained in finely disperse or colloidal form and are therefore preferably administered as their potassium salts (for example hetacillin) or lysinates (for example ibuprofen) or as their sodium salts (including ibuprofen and most of the other active ingredients mentioned above) in solution.

In contrast to the pure acids, the alkali metal salts of such active ingredients are generally freely water-soluble but often have a bitter taste and are precipitated from acidic solutions frequently in lumpy form and/or with foam formation; the same occurs in the case of solid dosage forms as a result of the gastric acid. These active ingredients therefore easily lead to irritation of the stomach walls.

To avoid these disadvantages, EP-A1-369 228 has already proposed granulating 100 parts by weight of a water-soluble ibuprofen salt with 200 to 1000 parts by weight of vehicle, 30 to 80 parts by weight of stabilizer (for example polyvinylpyrrolidone, "PVP") and 10 to 100 parts by weight of an alkali metal carbonate, and mixing the resulting granules with 100 to 400 parts by weight of the acid component. The aim here is to obtain the sodium salt in solution after dissolution of the effervescent tablet. This is achieved, inter alia, by virtue of the fact that the pH is in any case always above 6 in the case of the chosen composition. However, such a solution has an unpleasant taste, for example diclofenac sodium even has a bitter taste. In addition, very large amounts of PVP are required to prevent precipitation of the active ingredient as acid during effervescence.

DESCRIPTION OF THE INVENTION

It is therefore the object of the invention to provide effervescent mixtures of the type stated at the outset which ensure delayed precipitation of the active ingredients, but always in finely disperse or even colloidal form, under the action of acidic solutions or of the gastric acid. Furthermore, the resulting pH should be 4 to 5.5, at which effervescent solutions or suspensions are substantially more pleasant to drink.

According to the invention, this object is achieved for the first time, surprisingly, if both the soluble active ingredient salt and the acidic component of the effervescent system are passivated on the surface. Preferably, the alkali metal salt or lysinate coats the particles of the alkaline component of the effervescent system, for example sodium bicarbonate and/or sodium carbonate, and is covered in particular with further alkali metal carbonate. The active ingredient layers expediently also contain (per 100 parts by weight of active ingredient) at least 0.5 part by weight, preferably 1 to 3 parts by weight, of a surfactant, in particular docusate sodium or sodium laurylsulfate. Selecting the combination of very small amounts of stabilizer (or even no stabilizer at all) with surface-passivated components from the many possible formulations in the attempt to achieve the object was not obvious even to a person skilled in the art and required a large number of considerations.

In theory, individual acids can be obtained in micronized form. However, the precipitate according to the present invention is substantially finer than the form in which it would be possible to obtain a finely pulverulent active ingredient. The alkali metal salt or lysinate of the active ingredient acid first dissolves during the dissolution of the effervescent tablet or effervescent mixture, owing to the close contact with a sodium bicarbonate or a sodium carbonate particle; said active ingredient acid is precipitated only subsequently, in the solution prepared for drinking, by the acid component of the effervescent system, for example within 5 seconds, optionally even in colloidal form, but in any case in finely disperse form. However, the finely disperse particles remain suspended for a relatively long time and therefore give a liquid which is pleasant to drink.

In the stated finely disperse or even colloidal form, the acid no longer irritates the stomach walls, which are moreover protected by the buffer action of the effervescent system.

The active ingredients according to the invention are generally those which are intended to be absorbed not in the acidic medium of the stomach but in the alkaline medium of the intestine. The finely disperse form of the active ingredient in the solution also limits the passage through the stomach to about 15 to 20 minutes, so that immediate absorption can take place on entry into the pylorus and the intestine, owing to the very large surface area of finely disperse or almost colloidal acid particles of the active ingredient.

However, in order to achieve this effect, whereby the alkali metal salt or lysinate of the active ingredient goes into solution briefly on dissolution of the effervescent tablet and whereby only thereafter (after a delay) the active ingredient is precipitated in acid form by the remaining acidic solution, which may have a pH of 4 to 5.5, it is necessary to bind the alkali metal salt or lysinate of the active ingredient very intimately with the alkali metal carbonate, for example sodium bicarbonate or sodium carbonate, so that, at the instant of dissolution, alkaline protection is achieved around the particles, which delays the precipitation. This does not function if the active ingredient salt is merely mixed with an effervescent base, since in this case there is immediately contact with the acid, for example citric acid, at the instant of dissolution.

It is therefore expedient if pharmaceutically or toxicologically acceptable surfactants, such as, for example, docusate sodium or sodium laurylsulfate (dark-colored or pasty surfactants which are difficult to process are unsuitable), preferably in combination with binders, such as, for example, dextrin, polyvinylpyrrolidone or hydrocolloids, such as, for example, maltodextrin, are also added to the mixture. The suspension properties of the active ingredient acid in the liquid are greatly improved as a result. However, excessively large amounts of binder may cause undesirable foam formation and delay the dissolution of the effervescent tablet. The effect is also dependent on whether an aqueous or alcoholic solution is used.

It is therefore expedient if the mixture contains at least 1 part by weight, preferably 3 to 5, in particular not more than 20, parts by weight of binder or suspending agent, in particular polyvinylpyrrolidone. In contrast to the EP-A1 mentioned at the outset, only small amounts of binder are required here since the active ingredient acid is to be formed from its alkali metal salt or lysinate as early as during the dissolution of the effervescent tablet and is to be distributed in finely disperse form in the solution. A surfactant is therefore also preferably used in order to achieve better wetting of the acid particles during dissolution.

The binding of the active ingredient can be achieved in various ways:

1. The alkali metal salt or lysinate is dissolved and the solution is applied to sodium bicarbonate; drying is then carried out; the active ingredient salt crystallizes out on the surface of the sodium bicarbonate crystal.
2. The very finely powdered active ingredient is mixed with the sodium bicarbonate; both are agglomerated with a binder, for example dextrin. In this way, too, it is possible to achieve binding of the active ingredient salt to the sodium bicarbonate or sodium carbonate, since the binders do in fact slowly go into solution. Thus, the active ingredient first goes into solution as a salt and precipitated as the acid in finely disperse or colloidal form only after a delay, following the action and the reaction with the acid component of the effervescent system.

EXAMPLE 1

25 parts of diclofenac sodium are dissolved, with 10 parts of propylene glycol, 40 parts of sorbitol, 1 part of polyvinylpyrrolidone K30 and 0.5 part of a surfactant substance, in particular docusate sodium, in 40 parts of ethanol and 15 parts of water. The addition of a surfactant is advantageous because in particular the particles are immediately wet at the stage of the acid precipitation and agglomeration is therefore even more readily prevented. This solution is applied to 350 parts of sodium bicarbonate and thoroughly distributed; this is followed by the addition of 100 parts of sodium carbonate, which first absorbs water and only then goes into solution, in order to improve the alkaline protection. The material is then dried in vacuo and sieved to the desired particle size of, for example, 0.1 to 0.5 mm. The granules are then mixed with an acidic effervescent base consisting of a solid, edible, organic, surface-passivated acid and, if required, pressed to give tablets.

The surface passivation can be carried out in a manner known per se, for example as described in EP-B1-272 312 or WO93/00886. However, it is also possible to avoid the reaction between acid and carbonate in the passivation by coating or covering the surface of the acid crystals, for example of the citric acid, with a solution of sodium citrate and then applying to this coat sodium bicarbonate and/or sodium carbonate from a solution in the form of a coat. This application is particularly expediently effected in a vacuum mixing vessel and provides the best possible protection.

EXAMPLE 2

25 parts of diclofenac sodium are mixed with 350 parts of sodium bicarbonate and granulated together with the following solution: 15 parts of dextrin, 1 part of PVP and 0.5 part of a surfactant substance are dissolved in 20 parts of ethanol and 20 parts of water. The product is then dried, sieved to 0.1–0.5 mm, depending on requirements, and finally further treated as in Example 1.

EXAMPLE 3

1 part by weight of docusate sodium, 2 parts by weight of PVP and 100 parts by weight of naproxen sodium are dissolved in 400 parts by weight of 73% alcohol. 700 parts by weight of sodium bicarbonate are heated to 50° C. in a vacuum mixer while stirring; the solution is aspirated by means of a vacuum and homogeneously distributed while stirring, after which 150 parts by weight of sodium carbonate are applied to the wet granules. The granules are finally dried in vacuo while stirring, and sieved to 0.25 mm. Preparation of the acid granules surface-passivated with sodium bicarbonate:

1400 parts by weight of crystalline citric acid and 200 parts by weight of powdered citric acid are heated to 60° C. in a vacuum mixer while stirring and are wet with 6 parts by weight of water. Thereafter, 200 parts by weight of sodium bicarbonate are added and allowed to react at the surface of the citric acid, after which 50 parts by weight of sodium carbonate are added. The product is dried in vacuo while stirring.

The naproxen granules and the acid granules are mixed with one another, and sweetener, flavor and fillers are added. Mixing is then carried out for homogenization, and the granules are pressed to give tablets weighing 3.2 g.

When the effervescent tablet is introduced into water, the tablet dissolves in about 80 seconds, the naproxen being distributed in the solution in the form of a fine suspension, at a pH of 4–4.5.

We claim:

1. A preparation comprising:
    at least one acidic, insoluble or slightly soluble pharmaceutically active ingredient in the form of particles of a soluble alkali metal salt or lysinate of said active ingredient; and
    (ii) an effervescent system comprising particles of an alkaline component and particles of an acidic component, wherein
        said active ingredient is intimately mixed with at least a part of said alkaline component, wherein
        the quantity of said acidic component is sufficient to cause said active ingredient to precipitate from an aqueous solution into which the preparation has been introduced, and wherein
        the particles of said active ingredient and the particles of said acidic component are passivated on their respective surfaces by alkali metal or earth alkali metal carbonates or bicarbonates.

2. The preparation according to claim 1, wherein said active ingredient is a coating on the particles of said alkaline component, and the active ingredient coating is overcoated with alkali metal carbonate.

3. Preparation according to claim 2, wherein the amount of alkali metal carbonate is 150 to 400 parts per 100 parts of active ingredient.

4. Preparation according to claim 2, wherein said active ingredient is present mixed with a binder.

5. Preparation according to claim 4, wherein 3 to 5 parts by weight of binder are present per 100 parts of active ingredient.

6. Preparation according to claim 2, wherein said active ingredient is present mixed with surfactant.

7. Preparation according to claim 6, wherein 1 to 3 parts by weight of surfactant are present per 100 parts by weight of active ingredient.

8. Preparation according to claim 7 wherein said active ingredient is present mixed with 3 to 5 parts of binder per 100 parts of active ingredient.

9. Preparation according to claim 1, dissolved into an aqueous solution for oral administration, wherein the active ingredient has precipitated as the acid from said salt or lysinate and is present in finely dispersed form in said aqueous solution.

10. A preparation comprising:
(i) at least one acidic, insoluble or slightly pharmaceutically active ingredient in the form of particles of a soluble alkali metal salt or lysinate of the active ingredient; and
(ii) an effervescent system comprising particles of an alkaline component and of an acidic component, wherein
said active ingredient is intimately mixed with at least a part of said alkaline component, and wherein
the quantity of acidic component is sufficient to cause the active ingredient to precipitate from an aqueous solution into which the preparation has been introduced and provide a pH value of 4 to 5.5 to the aqueous solution.

11. The preparation according to claim 10, wherein said active ingredient is a coating on the particles of said alkaline component.

12. Preparation according to claim 11, wherein said active ingredient is present mixed with a binder.

13. Preparation according to claim 12, wherein 3 to 5 parts by weight of binder are present per 100 parts of active ingredient.

14. Preparation according to claim 11, wherein said active ingredient is present mixed with surfactant.

15. Preparation according to claim 14, wherein 1 to 3 parts by weight of surfactant are present per 100 parts by weight of active ingredient.

16. Preparation according to claim 15, wherein said active ingredient is present mixed with 3 to 5 parts of binder per 100 parts of active ingredient.

17. The preparation according to claim 16, wherein said active ingredient is ibuprofen, naproxen, diclofenac, butabarbital, phenobarbital, cefazolin, diatrizoate, ethacrynate, flurbiprofen, sulfacetamide or hetacillin, said binder is polyvinylpyrrolidone and said surfactant is docusate sodium or sodium lauryl sulfate.

18. The preparation according to claim 17, wherein said active ingredient coating is overcoated with alkali metal carbonate.

19. The preparation according to claim 18, wherein the amount of alkali metal carbonate is 150 to 400 parts per 100 parts of active ingredient.

* * * * *

UNITED STATES PATENT AND TRADEMARK OFFICE
CERTIFICATE OF CORRECTION

PATENT NO. : 5,593,693
DATED : January 14, 1997
INVENTOR(S) : Gerhard Gergely, et. al.

It is certified that error appears in the above-identified patent and that said Letters Patent is hereby corrected as shown below:

Title page, item [73], Assignee: should read Gerhard Gergely, Austria--.

Signed and Sealed this

Eighth Day of September, 1998

Attest:

BRUCE LEHMAN

Attesting Officer     Commissioner of Patents and Trademarks